US008728061B2

(12) United States Patent
Donitzky

(10) Patent No.: US 8,728,061 B2
(45) Date of Patent: May 20, 2014

(54) LASER SYSTEM THAT IS GENTLE ON THE EYES, FOR REFRACTIVE SURGERY

(75) Inventor: Christof Donitzky, Eschenau (DE)

(73) Assignee: Wavelight AG, Erlangen (DE)

( * ) Notice: Subject to any disclaimer, the term of this patent is extended or adjusted under 35 U.S.C. 154(b) by 724 days.

(21) Appl. No.: 12/532,058

(22) PCT Filed: Mar. 19, 2008

(86) PCT No.: PCT/EP2008/002233
§ 371 (c)(1),
(2), (4) Date: Mar. 19, 2010

(87) PCT Pub. No.: WO2008/113587
PCT Pub. Date: Sep. 25, 2008

(65) Prior Publication Data
US 2010/0280503 A1    Nov. 4, 2010

(30) Foreign Application Priority Data
Mar. 19, 2007  (EP) .................................. 07005598

(51) Int. Cl.
*A61B 18/18*  (2006.01)
(52) U.S. Cl.
USPC .................................. 606/5; 606/4
(58) Field of Classification Search
USPC .................................. 606/4, 5, 6
See application file for complete search history.

(56) References Cited

U.S. PATENT DOCUMENTS 3,715,683 A * 2/1973 Weber ............................ 372/68
5,206,697 A * 4/1993 Schwartz ..................... 356/5.06

(Continued)

FOREIGN PATENT DOCUMENTS

| JP | 2001-505094 | 4/2001 |
| WO | 8906519 | 7/1989 |
| WO | WO2006050424 | 5/2006 |
| WO | WO2006051364 | 5/2006 |

OTHER PUBLICATIONS

Ripin, D.J., "Generation of 20-fs Pulses by a Prismless Cr4+: YAG Laser," Optics Letters, Jan. 1, 2002, vol. 27, No. 1, 2002 Oprical Society of America, pp. 61-63.

(Continued)

*Primary Examiner* — Bill Thompson
*Assistant Examiner* — John R Downey
(74) *Attorney, Agent, or Firm* — Haynes and Boone, LLP

(57) ABSTRACT

Described is an eye treatment device having a radiation source, the light emitted by the radiation source having such a wavelength range that it brings about a reaction in a treatment region of an eye and is absorbed, at least partially, in at least one of the regions located behind same in the direction of the retina that are in front of the retina. The light emitted by the radiation source can have a wavelength range in which the treatment region is partially transmissive. The treatment region can be the cornea. The reaction brought about in the treatment region by the light can be an ablation of tissue. The reaction brought about in the treatment region by the light can also be a laser-induced optical perforation of tissue, which is also referred to as photo-disruption. The radiation source can be a laser source. The wavelength range of the light emitted by the radiation source is approximately 1600 nm to approximately 1700 nm, preferably approximately 1625 nm to approximately 1675 nm, most preferably approximately 1640 nm to approximately 1660 nm.

2 Claims, 3 Drawing Sheets

Wavelength in nm

Transmission of the cornea
— total
1 - - - direct 4.5 years
2 - - - direct 53 years

(56) References Cited

U.S. PATENT DOCUMENTS

| | | | |
|---|---|---|---|
| 5,348,551 A | 9/1994 | Spears et al. | |
| 5,656,186 A | 8/1997 | Mourou et al. | |
| 5,728,156 A * | 3/1998 | Gupta et al. | 623/6.26 |
| 5,984,916 A | 11/1999 | Lai | |
| 6,146,375 A | 11/2000 | Juhasz et al. | |
| 6,258,082 B1 | 7/2001 | Lin | |
| 6,325,792 B1 * | 12/2001 | Swinger et al. | 606/4 |
| 6,805,694 B2 * | 10/2004 | Donitzky | 606/5 |
| 7,548,367 B2 * | 6/2009 | Papuchon et al. | 359/333 |
| 7,675,674 B2 * | 3/2010 | Bullington et al. | 359/333 |
| 7,721,743 B2 | 5/2010 | Lenzner et al. | |
| 7,872,794 B1 * | 1/2011 | Minelly et al. | 359/341.31 |
| 7,998,135 B2 * | 8/2011 | Donitzky | 606/5 |
| 8,118,806 B2 * | 2/2012 | Triebel et al. | 606/5 |
| 2004/0176752 A1 | 9/2004 | Alfano et al. | |
| 2005/0149006 A1 | 7/2005 | Peyman | |
| 2008/0186551 A1 * | 8/2008 | Hanft et al. | 359/205 |
| 2009/0318906 A1 * | 12/2009 | Konig et al. | 606/5 |
| 2011/0040292 A1 * | 2/2011 | Riedel et al. | 606/5 |
| 2011/0137299 A1 * | 6/2011 | Donitzky et al. | 606/4 |
| 2011/0184394 A1 * | 7/2011 | Donitzky et al. | 606/5 |
| 2011/0295244 A1 * | 12/2011 | Mrochen et al. | 606/5 |
| 2012/0150160 A1 * | 6/2012 | Vogler et al. | 606/4 |

OTHER PUBLICATIONS

Korean Intellectual Property Office, "Notice of Office Action" for Korean Application No. 7021821/2009, mailed Feb. 28, 2013, 8 pages.

\* cited by examiner

Transmission of the cornea
— total
1 - - - direct 4.5 years
2 - - - direct 53 years

LASER SYSTEM THAT IS GENTLE ON THE EYES, FOR REFRACTIVE SURGERY

CROSS-REFERENCE TO RELATED APPLICATION

This application is a United States national phase application of international patent application number PCT/EP2008/002233, filed Mar. 19, 2008, which claims the benefit of European patent application number EP 07005598.3, filed Mar. 19, 2007, the disclosure of which is incorporated herein by reference.

BACKGROUND

The invention relates to a laser system that is gentle on the eye, for refractive surgery, and to a refractive treatment method that is gentle on the eye.

In ophthalmology, "refractive surgery" by means of lasers is understood to be the interaction of laser radiation with parts of the eye, in order to alter the refractive properties of the eye, and consequently its imaging properties, for the purpose of eliminating, or at least alleviating, imaging defects.

DETAILED DESCRIPTION

A particularly important example of refractive surgery is the correction of the defective vision of an eye by means of the LASIK technique. In the case of LASIK according to the prior art, the cornea is first cut open laterally by means of, for example, a microkeratome, and the thus resulting small cover (also termed flap) is folded to the side. In the thus exposed stroma of the cornea, laser radiation is used to effect a so-termed ablation, i.e. the removal of tissue in accordance with a calculated ablation profile. The small cover is subsequently folded back, and a relatively painless and rapid healing process ensues. Following this procedure, the cornea has different imaging properties, and the defective vision has been remedied or reduced.

Usually, in the case of the prior art, the lateral incision into the cornea, described above, is effected by means of a so-termed microkeratome, i.e. an oscillating mechanical cutting edge. More recently, use has also been made of so-termed femtosecond microkeratomes, in which femtosecond laser pulses are focussed in the tissue of the cornea, in order to produce therein, by means of closely adjacent focal points of the radiation, a so-termed laser-induced perforation, or so-termed laser-induced photo-disruptions in the corneal tissue, which are performed in the corneal tissue in such a way that a cut is ultimately produced, as in the case of a mechanical microkeratome.

Depending on the nature of the treatment (e.g. incision or ablation) and/or the tissue type, laser radiation of differing wavelengths and/or pulse durations is used in laser-optical eye surgery. For the application of cuts (incision) in the cornea (for instance, for the preparation of a flap), it is usual to use laser radiation in the range from approximately 340 to 350 nm or in the near-infrared (NIR) wavelength range, for example between 1000 and 1100 nm, with a pulse duration in the femtosecond range. Such a system is also referred to as a femtosecond microkeratome. By contrast, for photoablation of stroma tissue, laser radiation in the ultraviolet wavelength range, for example 193 nm, is generally used, wherein the pulse duration used can also be longer, as far as into the nanosecond range.

In general, in the case of cutting of the flap by means of the femtosecond laser, there occurs an energy transmission of approximately 40% through the cornea. This energy transmitted through the cornea can result, in the eye, in a strong radiation impact that is manifested in the patient as a side-effect, for example as the so-termed transient light syndrome (TLS), over several months.

If a visible wavelength is used in the case of cutting of the flap by means of a femtosecond laser, for example a titanium-sapphire laser having a wavelength of 710 nm to 810 nm, or a frequency-doubled infrared system having a wavelength of approximately 517 nm, there occurs during the operation process a visual stressing of the patient that is unacceptable.

UV femtosecond laser systems having a frequency tripling of infrared radiation emit a wavelength of approximately 345 nm in that, for example, the third harmonic is produced. In the case of this wavelength, an extremely efficient conversion of the laser-beam energy is produced during the photo-disruption process. Nevertheless, approximately 5% of the energy enters further into the eye and is absorbed in the lens. Further, there is produced a blue-light fluorescence with a fluorescence maximum at 440.

nm, which corresponds to the peak of the so-termed blue-light hazard effect (blue-light hazard) and results, most importantly, in damage to the retina.

WO 89/06519 A2 discloses the use of a wavelength in the range from 1400 to 1800 nm in the case of intrastromal keratomileusis for the purpose of modifying the curvature of the cornea.

U.S. Pat. No. 6,258,082 B1 discloses a diode laser having a wavelength of 980 nm, 1.5 µm and 1.9 µm, as well as a diode-pumped Er:YAG laser having a wavelength of approximately 2.94 µm. The radiation emitted by this laser is applied in the case of photorefractive keratectomy, phototherapeutic keratectomy, intrastromal photokeratectomy, LASIK and LASE.

U.S. Pat. No. 5,656,186 is concerned with ablation and a laser-induced perforation of the cornea by means of laser pulses of the range from 150 fsec to 7 nsec. A wavelength of 770 nm is used for this purpose.

The publication "Generation of 20-fs pulses by a prismless $Cr^{4+}$:YAG laser" Ripin et alteri, Optics Letter, Vol. 27, No. 1, 1 Jan. 2002 discloses a $Cr^{4+}$:YAG laser in which pulses shorter than 20 fsec were measured in the case of a prismless laser. The pulses had their maximum at 1450 nm, and in a range from 1310 nm to 1500 nm the intensity was greater than half of the maximum. By means of a logarithmic scale it was possible to observe a spectrum from 1140 nm to 1700 nm, which was the limit of the spectral instrument used.

It is an object of the invention to create an eye treatment device that is gentle on the eye.

The object is achieved by an eye treatment device according to Claim 1. The light emitted by the radiation source has such a wavelength range that it brings about a reaction in a treatment region of an eye and is absorbed, at least partially, in at least one of the regions located behind same in the direction of the retina. This has the advantage that the light radiation passing through the treatment region is absorbed, and damage to the structures located behind the treatment region can be prevented.

The light emitted by the radiation source can have a wavelength range in which the treatment region is partially transmissive.

The treatment region can be the cornea. The light radiation passing through the cornea can be absorbed, for example, in the aqueous humour. Consequently, damage to structures located behind the aqueous humour, for example the iris, the lens, the vitreous body and the retina, can be prevented.

The reaction brought about in the treatment region by the light can be an ablation of tissue. The ablation of tissue enables the cornea to be reshaped, in order to correct any defective vision. The reaction brought about in the treatment region by the light can also be a laser-induced optical perforation of tissue, which is also referred to as photo-disruption. The laser-induced perforations, or the photo-disruptions, can be used to produce a cut in the cornea.

The radiation source can be a laser source. A femtosecond laser source can be used to produce the laser-induced perforations.

The wavelength range of the light emitted by the radiation source is approximately 1600 nm to approximately 1700 nm, preferably approximately 1625 nm to approximately 1675 nm, most preferably approximately 1640 nm to approximately 1660 nm. In these wavelength ranges the cornea is transmissive of light and the light passing through the cornea is absorbed in the aqueous humour, as a result of which damage to the structures located behind the aqueous humour, for example the iris, the lens, the vitreous body or the retina, can be prevented. In particular, the systems Co:MgF$_2$ and Cr:YAG are possibilities as femtosecond laser systems for the wavelength range 1600-1700 nm.

A method for treating the eye with light has such a wavelength range that it brings about a reaction in a treatment region and is absorbed, at least partially, in at least one of the regions located behind same in the direction of the retina. This has the advantage that the light radiation emerging from the treatment region is absorbed, and damage to the structures located behind the treatment region can be prevented.

The treatment region can be substantially transmissive in the wavelength range. The treatment region can be the cornea. As mentioned previously, the light radiation passing through the cornea can be absorbed, for example, in the aqueous humour. Consequently, damage to structures located behind the aqueous humour, for example the iris, the lens, the vitreous body and the retina, can be prevented.

The reaction brought about in the treatment region by the light can be an ablation of tissue. The reaction brought about in the treatment region by the light can also be a laser-induced optical perforation of tissue. The radiation source can be a laser source.

The wavelength range in the case of the method is approximately 1600 nm to approximately 1700 nm, preferably approximately 1625 nm to approximately 1675 nm, most preferably approximately 1640 nm to approximately 1660 nm. As mentioned previously, in these wavelength ranges the cornea is transmissive of light and the light passing through the cornea is absorbed in the aqueous humour, as a result of which damage to the structures located behind the aqueous humour, for example the iris, the lens, the vitreous body and the retina, can be prevented.

The invention is now described in greater detail with reference to the appended figures.

Radiation sources suitable for ablation and incision are known to the specialist in the field of ophthalmology, in particular refractive surgery. These radiation sources include laser light sources. As mentioned at the beginning, pulse durations in the femtosecond range are used for incision, and longer pulse durations are used for ablation. So-termed frequency multipliers can be used to adapt the wavelength of the laser to the application. Such laser systems are known to the specialist in the art, and need not be described in greater detail.

Figure 1:
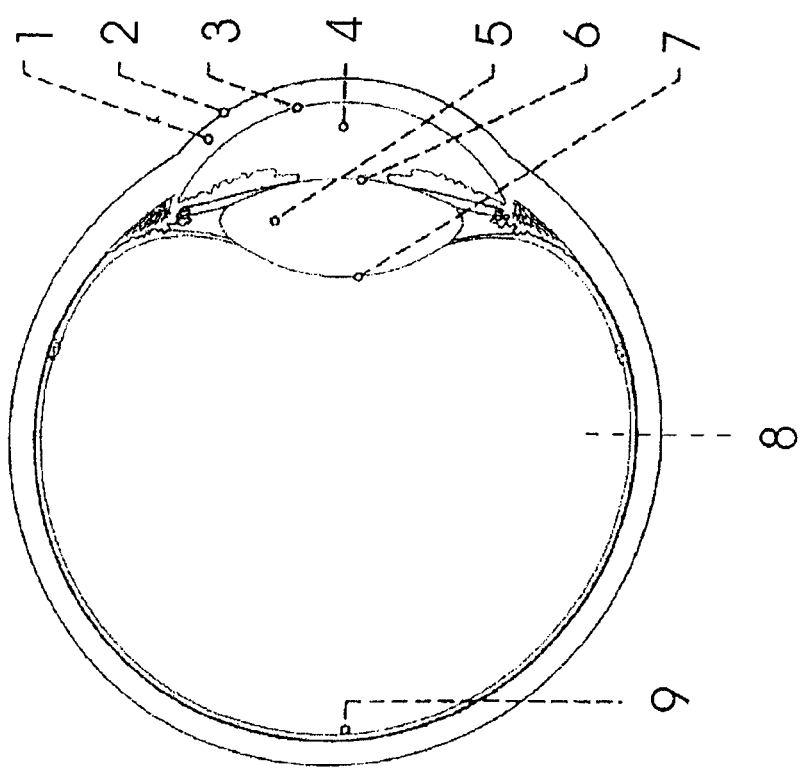
FIG. 1 shows an eye model according to Gullstrand-Le Grand.

FIG. 1 shows an eye model by Gullstrand-Le Grand. The cornea 1 has a front surface 2 and a rear surface 3. Located behind the rear surface 3 of the cornea 1 is the aqueous humour 4. Located behind the aqueous humour 4 is the lens 5, having a front surface 6 and a rear surface 7. Adjoining behind the lens is the vitreous body 8. Located behind the vitreous body 8 is the retina 9. The light goes into the eye through the cornea 1 and is imaged onto the retina 9.

As mentioned at the beginning, in the case of refractive surgery a laser-induced optical perforation is used to produce a cut in the cornea 1, by means of a femtosecond laser. It is understood that the laser radiation is not fully absorbed through the laser-induced perforation in the cornea 1. In the case of eye treatment devices of the prior art, the portion of the laser radiation not absorbed in the cornea 1 passes through the aqueous humour 4, the lens 5 and the vitreous body 8, and strikes the retina 9. Depending on the wavelength used, the patient may have side-effects, for example the previously mentioned transient light syndrome or damage to the retina 9 resulting from the blue-light hazard effect.

Likewise, in the case of ablation of tissue in the cornea 1 for the purpose of correcting defective vision, in the case of eye treatment devices of the prior art the portion of the radiation not absorbed in the cornea 1 can pass through the aqueous humour 4, the lens 5 and the vitreous body 8, and strike the retina 9. In this case, likewise, the previously described side-effects occur, depending on the wavelength used. By contrast, the radiation of the excimer laser, having a wavelength of 193 nm, is absorbed fully in the cornea.

Figure 2:
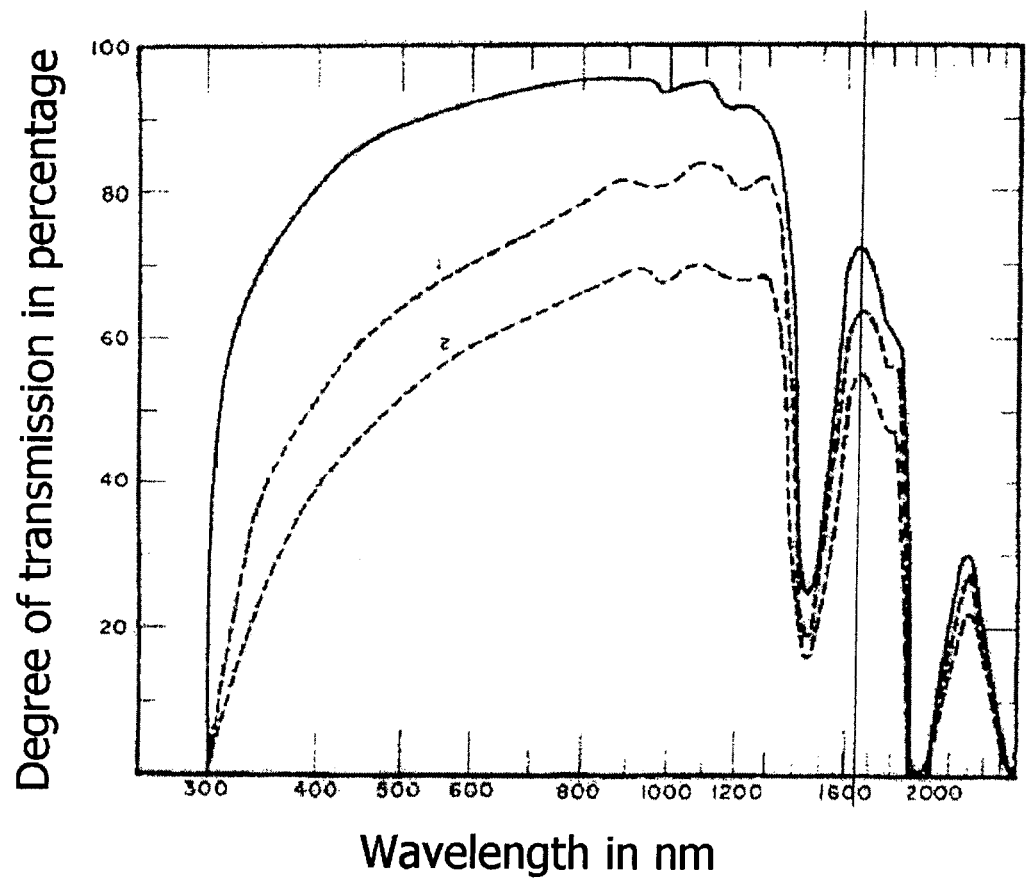
FIG. 2 is a diagram representing the transmission of the cornea.
Figure 3:
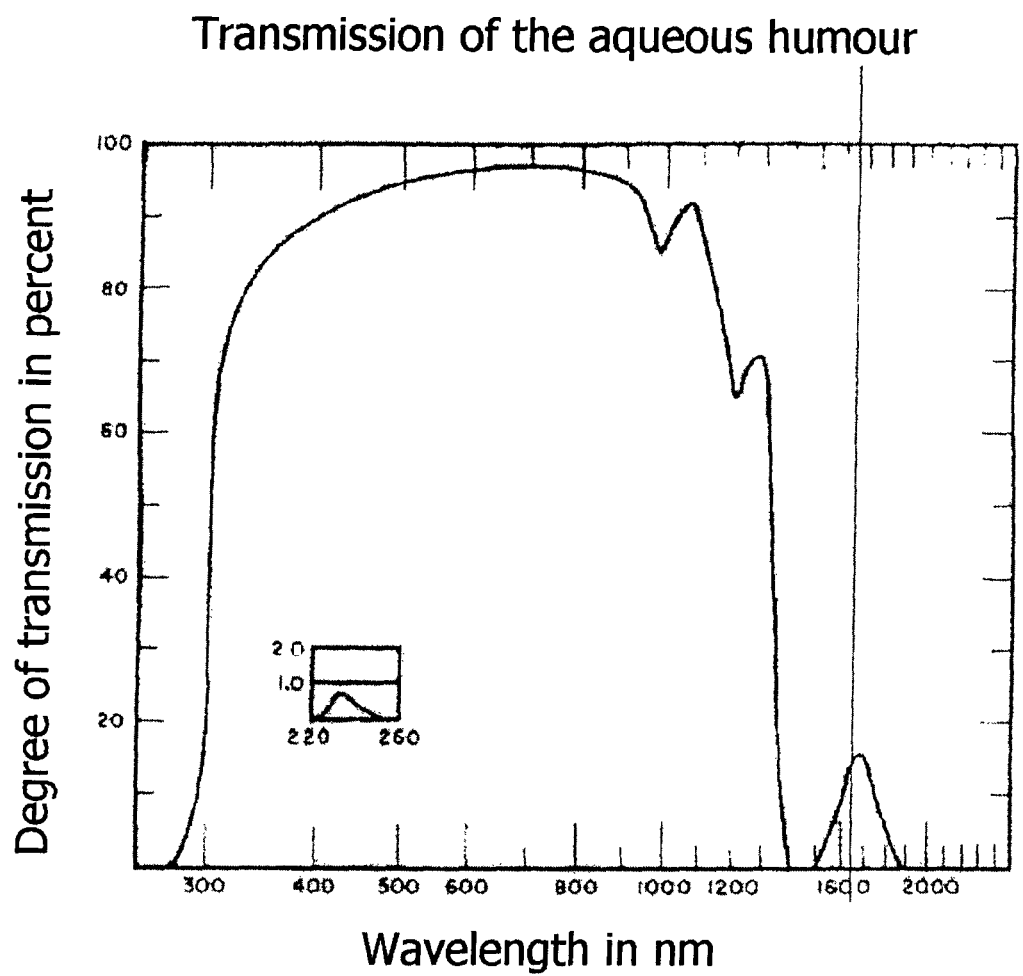
FIG. 3 is a diagram representing the transmission of the aqueous humour.

FIG. 2 is a diagram representing the degree of transmission of the cornea. FIG. 3 is a diagram representing the degree of transmission of the aqueous humour. In FIG. 2, the unbroken line shows the total transmission of the cornea 1, which transmission was ascertained from six eyes. The curve denoted by 1 in FIG. 2 shows the direct transmission in the case of an eye of a child of 4½ years of age, and the curve denoted by 2 shows the direct transmission in the case of an eye of a person of 53 year of age.

In the case of both incision and ablation, the cornea is the aforementioned treatment region. A treatment is to be possible, not only on the surface of the cornea 1, but also in deeper regions of the cornea 1. Consequently, the wavelength range selected for the treatment is to be selected in such a way that the cornea 1 is partially transmissive in this wavelength range. Suitable for this purpose, according to FIG. 2, are, on the one hand, the wavelength range from 300 nm to 1300 nm and the wavelength range from 1600 nm to 1700 nm.

It was realized that the previously described side-effects can be prevented if the radiation not absorbed in the treatment region, i.e. the cornea, is absorbed in a region located behind same. In this case, the radiation not absorbed in the cornea cannot reach, for example, the lens and/or the retina 9.

It is proposed, for the purpose of treating the cornea 1, a wavelength range lies from approximately 1600 nm to 1700 nm. If the radiation not absorbed in the cornea 1 to use in the aqueous humour approximately 1700 nm, since in this range the aqueous humour 4 has a comparatively low transmission. Consequently, the absorption of the radiation not absorbed in the cornea 1 occurs in a region that absorbs as close as possible to the cornea 1, it cannot pass through the iris, the lens 5 and the vitreous body 8 and strike the retina 9, or it can do so only having been weakened by the absorption in the aqueous humour 4. As a result, damage to or impairment of other regions of the eye, and the previously described side-effects, are prevented to a large extent.

The invention claimed is:

1. Method for treating a cornea of an eye, comprising the following steps:
   providing a Cr:YAG laser radiation source that emits a laser beam having a wavelength between 1640 nm and 1660 nm such that a treatment region of a cornea of an eye to be treated is at least partially transmissive to the laser beam to allow laser-induced optical breakdown of tissue in the cornea of the eye and absorption of the laser beam within an aqueous humour of the eye positioned behind the cornea;
   directing the laser beam from the Cr:YAG laser radiation source having a wavelength between 1640 nm and 1660 nm onto the eye to be treated with a pulse width in the femtosecond range such that the laser beam brings about a laser-induced optical perforation in the tissue of the cornea of the eye that produces a cut in the cornea defining a flap having a hinge defined by remaining material in the cornea such that the flap can be folded along the hinge to expose a stroma of the cornea, wherein the laser beam is absorbed in the cornea and in the aqueous humour of the eye located between the cornea and a retina of the eye such that the laser beam does not pass through the aqueous humour to damage the iris, lens, vitreous body, or retina of the eye when producing the cut defining the flap; and
   directing a laser beam from the Cr:YAG laser radiation source having a wavelength between 1640 nm and 1660 nm onto the exposed stroma of the cornea with a pulse width longer than those used for the producing the cut defining the flap such that the laser beam ablates tissue to reshape the cornea to correct defective vision of the eye to be treated, wherein the laser beam is absorbed in the cornea and in the aqueous humour of the eye located between the cornea and a retina of the eye such that the laser beam does not pass through the aqueous humour to damage the iris, lens, vitreous body, or retina of the eye when reshaping the cornea.

2. A method of treating a cornea of an eye, comprising:
   providing a Co:MgF$_2$ laser radiation source that emits a laser beam having a wavelength between 1640 nm and 1660 nm such that a treatment region of a cornea of an eye to be treated is at least partially transmissive to the laser beam to allow laser-induced optical breakdown of tissue in the cornea of the eye and absorption of the laser beam within an aqueous humour of the eye positioned behind the cornea;
   directing the laser beam from the Co:MgF$_2$ laser radiation source having a wavelength between 1640 nm and 1660 nm onto the eye to be treated with a pulse width in the femtosecond range such that the laser beam brings about a laser-induced optical perforation in the tissue of the cornea of the eye that produces a cut in the cornea defining a flap having a hinge defined by remaining material in the cornea such that the flap can be folded along the hinge to expose a stroma of the cornea, wherein the laser beam is absorbed in the cornea and in the aqueous humour of the eye located between the cornea and a retina of the eye such that the laser beam does not pass through the aqueous humour to damage the iris, lens, vitreous body, or retina of the eye when producing the cut defining the flap; and
   directing a laser beam from the Co:MgF$_2$ laser radiation source having a wavelength between 1640 nm and 1660 nm onto the exposed stroma of the cornea with a pulse width longer than those used for the producing the cut defining the flap such that the laser beam ablates tissue to reshape the cornea to correct defective vision of the eye to be treated, wherein the laser beam is absorbed in the cornea and in the aqueous humour of the eye located between the cornea and a retina of the eye such that the laser beam does not pass through the aqueous humour to damage the iris, lens, vitreous body, or retina of the eye when reshaping the cornea.

* * * * *